(12) United States Patent
Stimits et al.

(10) Patent No.: US 11,737,988 B2
(45) Date of Patent: Aug. 29, 2023

(54) ANTI-HYPERTENSIVE AND CHOLESTEROL-LOWERING FIXED-DOSE COMBINATION AND METHOD OF MANUFACTURE

(71) Applicant: CardioPharma, Inc., Wilmington, NC (US)

(72) Inventors: Roy A. Stimits, Hampstead, NC (US); Daniel Tyree Gregory, Jr., Hampstead, NC (US); Wayne L. Whittingham, Wilmington, NC (US); Stephan Dale Glenn, Weston, FL (US); David P. Hause, Carrboro, NC (US)

(73) Assignee: CardioPharma, Inc., Wilmington, NC (US)

( * ) Notice: Subject to any disclaimer, the term of this patent is extended or adjusted under 35 U.S.C. 154(b) by 0 days.

(21) Appl. No.: 16/620,431

(22) PCT Filed: Apr. 17, 2019

(86) PCT No.: PCT/US2019/027936
§ 371 (c)(1),
(2) Date: Dec. 6, 2019

(87) PCT Pub. No.: WO2020/214163
PCT Pub. Date: Oct. 22, 2020

(65) Prior Publication Data
US 2020/0330391 A1 Oct. 22, 2020

(51) Int. Cl.
*A61K 9/20* (2006.01)
*A61K 9/16* (2006.01)
(Continued)

(52) U.S. Cl.
CPC .......... *A61K 9/2095* (2013.01); *A61K 9/2893* (2013.01); *A61K 31/366* (2013.01);
(Continued)

(58) Field of Classification Search
None
See application file for complete search history.

(56) References Cited

U.S. PATENT DOCUMENTS 6,576,256 B2   6/2003   Liang et al.
6,669,955 B2  12/2003   Chungi et al.
(Continued)

FOREIGN PATENT DOCUMENTS

CN     101590232 A    12/2009
EP       2322175 A1    5/2011
(Continued)

OTHER PUBLICATIONS

International Search Report and Written Opinion for PCT/US2019/027936, dated Jul. 23, 2019.
(Continued)

*Primary Examiner* — Lakshmi S Channavajjala
(74) *Attorney, Agent, or Firm* — Karen Canaan; CanaanLaw, P.C.

(57) ABSTRACT

Disclosed is a method of manufacturing a cardiovascular fixed-dose combination pharmaceutical dosage form that includes an anti-hypertensive active agent, a cholesterol-lowering active agent, and optionally, an enteric-coated aspirin or platelet inhibitor. The fixed-dose combination is prepared with at least two granulation solutions that are free of citric acid and enhance the aqueous solubility of the cholesterol-lowering agent in fixed-dose combination. The active agents in the resulting dosage form, which is also free of citric acid, have the same strength and release profiles as the same active agents prepared as a single formulation.

71 Claims, 7 Drawing Sheets

(51) Int. Cl.

| | |
|---|---|
| *A61K 45/06* | (2006.01) |
| *A61K 31/401* | (2006.01) |
| *A61K 31/366* | (2006.01) |
| *A61K 9/28* | (2006.01) |
| *A61K 31/616* | (2006.01) |
| *A61K 9/48* | (2006.01) |

(52) U.S. Cl.
CPC .......... *A61K 31/401* (2013.01); *A61K 31/616* (2013.01); *A61K 9/4891* (2013.01); *A61K 45/06* (2013.01)

(56) References Cited

U.S. PATENT DOCUMENTS

| | | | |
|---|---|---|---|
| 7,374,779 | B2 | 5/2008 | Chen et al. |
| 9,789,187 | B2 * | 10/2017 | Khamar ................ A61P 9/12 |
| 2004/0137054 | A1 * | 7/2004 | Hager .................. A61K 45/06 514/474 |
| 2005/0026992 | A1 | 2/2005 | Sasmal et al. |
| 2008/0161296 | A1 | 7/2008 | Davis et al. |
| 2010/0234442 | A1 | 9/2010 | Duarte-Vazquez et al. |
| 2012/0045505 | A1 | 2/2012 | Sasmal et al. |
| 2013/0078284 | A1 | 3/2013 | Ju et al. |
| 2021/0145754 | A1 * | 5/2021 | Ding ..................... A61P 3/06 |

FOREIGN PATENT DOCUMENTS

| | | | |
|---|---|---|---|
| EP | 3090744 | A1 | 11/2016 |
| WO | WO-2006085128 | A1 * | 8/2006 ............. A61K 45/06 |

OTHER PUBLICATIONS

Aerosil(R) and Aeroperl(R) Colloidal Silicon Dioxide for Pharmaceuticals, Evonik Industries, Technical Information T1 1281, 2015.
Gautam et al., Fixed dose drug combinations (FDCs): rational or irrational: a point of view, British Journal of Clinical Pharmacology 65(5):795-796 (2007).
Gupta et al., Fixed dose drug combinations: Issues and challenges in India, Indian Journal of Pharmacology 48(4):347-349 (2016).
Herman et al., Angiotensin Converting Enzyme Inhibitors (ACEI), StatPearls Publishing LLC, 2019 (NCBI Bookshelf ID: NK431051; PMID (PubMedID): 28613705).
Kaplan, Fixed Dose Combinations as an Innovative Delivery Mechanism, Background Paper on Priority Medicines for Europe and the World "A Public Health Approach to Innovation," 2014.
Naveed, IntechOpen (Open Access Book), Chapter 11, Interaction Studies of ACE Inhibitors with Statins, 2015 (available at http://dx.doi.org/10.5772/59491).
Savjani et al., Drug Solubility: Importance and Enhancement Techniques, ISRN Pharmaceuticals, Article ID 195727 (2012).
Schachter, Chemical, pharmacokinetic and pharmacodynamic properties of statins: an update, Fundamentals & Clinical Pharmacology 19:117-125 (2004).
Speakerman, Introduction to X-Ray Powder Diffraction Data Analysis, Publication from the Center for Materials Science and Engineering, MIT (2012).
Stahly, Cocrystals: A Regulatory Rebirth, Whitepaper from Triclinic Labs (2016).
Tashko, Fat vs. water soluble statins, Publication from GT Health (2017) (available at gertitashkomd.com/blog/2017/7/20/fat-vs-water-soluble-statins).
Supplementary European Search Report for European counterpart patent application No. EP 19924674.5 dated Nov. 10, 2022 (3 pages).

* cited by examiner

ANTI-HYPERTENSIVE AND CHOLESTEROL-LOWERING FIXED-DOSE COMBINATION AND METHOD OF MANUFACTURE

TECHNICAL FIELD

The present invention relates generally to fixed-dose combination pharmaceuticals and more specifically to stable pharmaceutical dosage forms comprising anti-hypertensive and cholesterol-lowering active agents.

BACKGROUND OF THE INVENTION

Patients that are at risk of cardiovascular events are often administered more than one medication to keep risk factors under control. It is known that patient compliance drops when more than one oral pharmaceutical dosage form is required to treat a condition; thus, combination pharmaceuticals, also known as fixed-dose combinations, having at least two cardiovascular treatment medications is desirable from a treatment perspective. Fixed-dose combinations for any two active agents often have problems, including (i) pharmacodynamic mismatch between the individual drugs where one drug has an additive/antagonistic effect to another drug in the combination, leading to reduced efficacy or enhanced toxicity for the combination; (ii) pharmacokinetic mismatch between two drugs leading to peak efficiency of the drugs at different times; (iii) chemical incompatibility between the two drugs leading to decreased shelf-life of the pharmaceutical; (iv) chemical interactions during common metabolizing pathways leading to the ineffectiveness of one or more of the drugs in the combination; and (v) dosing titration limitations of the individual drugs.

For cardiovascular treatment, angiotensin-converting enzyme inhibitors (also known as "ACE inhibitors") and HMG-CoA reductase inhibitors (also known as "statins") are frequently administered to patients as separate drugs. ACE inhibitors block the converting enzyme of angiotensin, which is responsible for cleavage from angiotensin I, which is a decapeptide, to angiotensin II, which is an octapeptide, and lower the blood pressure by reducing peripheral vascular resistance. ACE inhibitors also decrease aldosterone secretion and the resulting sodium and water retention. The oral bioavailability of ACE inhibitors ranges from 13% to 95%. Most ACE inhibitors are administered as pro-drugs that remain inactive until esterified in the liver. Statins are hypolipidemic agents that are used for treatment of hyperlipidemia. Statins are highly effective at enhancing HDL levels while reducing total cholesterol, LDL cholesterol, apolipoprotein B, and triglycerides.

Combining ACE inhibitors and statins into a fixed-dose combination has been problematic because ACE inhibitors undergo decomposition reactions in the presence of acids and bases, the latter of which are used to stabilize statins. Thus, in the presence of stabilized statin, an ACE inhibitor may decompose to such an extent that even after a short storage period, the content of decomposition products in the ACE inhibitor/statin fixed-dose combination is so high that the permissible limit of degradation products is exceeded. In view of the foregoing, there remains a need in the art for stable fixed-dose combinations for treating patients at risk of cardiovascular events.

SUMMARY OF THE INVENTION

The disclosure provided herein overcomes the need in the art by providing a method for preparing a combination dosage form comprising an anti-hypertensive active agent and a cholesterol-lowering active agent, wherein both the cholesterol-lowering and the anti-hypertensive active agents are stable and have release profiles that are unchanged from the single dosage form of the individual active agents.

In one embodiment, there is disclosed a method comprising: blending a cholesterol-lowering drug and an anti-hypertensive drug in a first granulation solution comprising a preservative to form a first granulated mixture; adding a second granulation solution comprising a binder to the first granulated mixture to form a second granulated mixture, wherein the blending of the cholesterol-lowering drug and the anti-hypertensive drug in the first and second granulation solutions enhances aqueous solubility of the cholesterol-lowering drug; drying the second granulated mixture to form individual granules, wherein each of the individual granules contains the cholesterol-lowering drug, the anti-hypertensive drug, or a combination of the cholesterol-lowering drug and the anti-hypertensive drug; and forming a pharmaceutical dosage form comprising the individual granules.

In another embodiment, there is disclosed a method comprising: blending a cholesterol-lowering drug in a first granulation solution comprising a preservative to form a first granulated mixture; blending an anti-hypertensive agent in a second granulation solution comprising a binder to form a second granulated mixture; blending the first and the second granulated mixtures together to form a third granulated mixture, wherein the blending of the cholesterol-lowering drug and the anti-hypertensive drug in the third granulated mixture enhances aqueous solubility of the cholesterol-lowering drug; drying the third granulated mixture to form individual granules, wherein each of the individual granules contains the cholesterol-lowering drug, the anti-hypertensive drug, or a combination of the cholesterol-lowering drug and the anti-hypertensive drug; and forming a pharmaceutical dosage form comprising the individual granules.

In a further embodiment, there is disclosed a method comprising: blending a cholesterol-lowering drug in a first granulation solution comprising a preservative to form a first granulated mixture; adding a granulated anti-hypertensive drug to the first granulated mixture to form a second granulated mixture; adding a second granulation solution comprising a binder to the second granulated mixture to form a third granulated mixture, wherein the blending of the cholesterol-lowering drug and the anti-hypertensive drug in the third granulated mixture enhances aqueous solubility of the cholesterol-lowering drug; drying the third granulated mixture to form individual granules, wherein each of the individual granules contains the cholesterol-lowering drug, the anti-hypertensive drug, or a combination of the cholesterol-lowering drug and the anti-hypertensive drug; and forming a pharmaceutical dosage form comprising the individual granules.

In another embodiment, the preservative is selected from the group consisting of parabens, acids and their salts, quaternary ammonium compounds, alcohols, biguanides, phenols, phenolic antioxidants, and combinations thereof.

In a further embodiment, the preservative is solubilized in a liquid selected from the group consisting of water, ethanol, isopropanol, and combinations thereof.

In another embodiment, the first granulation solution comprises butylated-hydroxy-anisole (BHA) solubilized in ethanol.

In a further embodiment, the binder is selected from the group consisting of saccharides, polysaccharides and derivatives, sugar alcohols, proteins, synthetic polymers, and combinations thereof.

In another embodiment, the binder is solubilized in a liquid selected from the group consisting of water, ethanol, isopropanol, and combinations thereof.

In a further embodiment, the second granulation solution comprises polyvinyl pyrrolidone (PVP) solubilized in a water and ethanol solution.

In another embodiment, the first granulation solution, the second granulation solution, and the pharmaceutical dosage form are free of citric acid.

In a further embodiment, the anti-hypertensive drug is selected from the group consisting of angiotensin-converting enzyme (ACE) inhibitors, angiotensin receptor inhibitors, and beta blockers.

In another embodiment, the ACE inhibitors are selected from the group consisting of benazepril, captopril, enalapril, fosinopril, lisinopril, moexipril, perindopril, quinapril, ramipril, trandolapril, and combinations thereof.

In a further embodiment, the angiotensin receptor inhibitors are selected from the group consisting of azilsartan, candesartan, eprosartan, irbesartan, telmisartan, valsartan, losartan, olmesartan, entresto, byvalson, and combinations thereof.

In another embodiment, the beta blockers are selected from the group consisting of betaxolol, pindolol, acebutolol, atenolol, bisoprolol fumarate, carvedilol, esmolol, labetalol, metoprolol, nadolol, nebivolol, and combinations thereof.

In a further embodiment, the cholesterol-lowering drug is a statin selected from the group consisting of atorvastatin, fluvastatin, lovastatin, pravastatin, pitavastatin, simvastatin, rosuvastatin, and combinations thereof.

In another embodiment, the cholesterol-lowering drug is a non-statin selected from the group consisting of ezetimibe, gemfibrozil, fenofibric acid, lomitapide, and combinations thereof.

In a further embodiment, the anti-hypertensive drug is an ACE inhibitor and the cholesterol-lowering drug is a statin.

In another embodiment, the anti-hypertensive drug is lisinopril and the cholesterol-lowering drug is simvastatin.

In a further embodiment, the anti-hypertensive drug is present in the pharmaceutical dosage form in a range of 1 mg to 160 mg per unit dose.

In another embodiment, the cholesterol-lowering drug is present in the pharmaceutical dosage form in a range of 1 mg to 160 mg per unit dose.

In a further embodiment, the pharmaceutical dosage form further comprises enteric coated aspirin or an enteric coated platelet inhibitor.

In another embodiment, the enteric coated platelet inhibitor is selected from the group consisting of clopidogrel, ticagrelor, prasugrel, dipyridamole, ticlopidine, eptifibatide, and combinations thereof.

In a further embodiment, the enteric coated aspirin or the enteric coated platelet inhibitor is in a concentration of 25 mg to 325 mg per unit dose.

In another embodiment, the enteric coated aspirin is in a concentration of 81 mg per unit dose.

In a further embodiment, the pharmaceutical dosage form is a capsule.

In another embodiment, the pharmaceutical dosage form further comprises enteric coated aspirin tablets or an enteric coated platelet inhibitor encased within the capsule.

In a further embodiment, the pharmaceutical dosage form is a tablet.

In another embodiment, the tablet comprises a core and an immediate release outer layer, wherein the core of the tablet is enteric coated aspirin and the immediate release outer layer is comprised of the individual granules comprising the anti-hypertensive drug, the cholesterol-lowering drug, or a combination of the anti-hypertensive drug and the cholesterol-lowering drug.

In a further embodiment, the tablet comprises a core and an immediate release outer layer, wherein the core of the tablet is an enteric coated platelet inhibitor and the immediate release outer layer is comprised of the individual granules comprising the anti-hypertensive drug, the cholesterol-lowering drug, or a combination of the anti-hypertensive drug and the cholesterol-lowering drug.

In another embodiment, the method further comprises administering a single dosage of the pharmaceutical dosage form to an individual in need of an anti-hypertensive drug and a cholesterol-lowering drug once per 24-hour period.

Additional aspects and embodiments of the invention will be provided, without limitation, in the detailed description of the invention that is set forth below.

BRIEF DESCRIPTION OF THE DRAWINGS

FIGS. 4A-4D are graphs showing XRPD patterns of fixed-dose simvastatin:lisinopril combinations having the following ratios of simvastatin:lisinopril: 1:1 (FIG. 4A); 4:1 (FIG. 4B); and 2:1 (FIG. 4C).

DETAILED DESCRIPTION OF THE INVENTION

Figure 1:
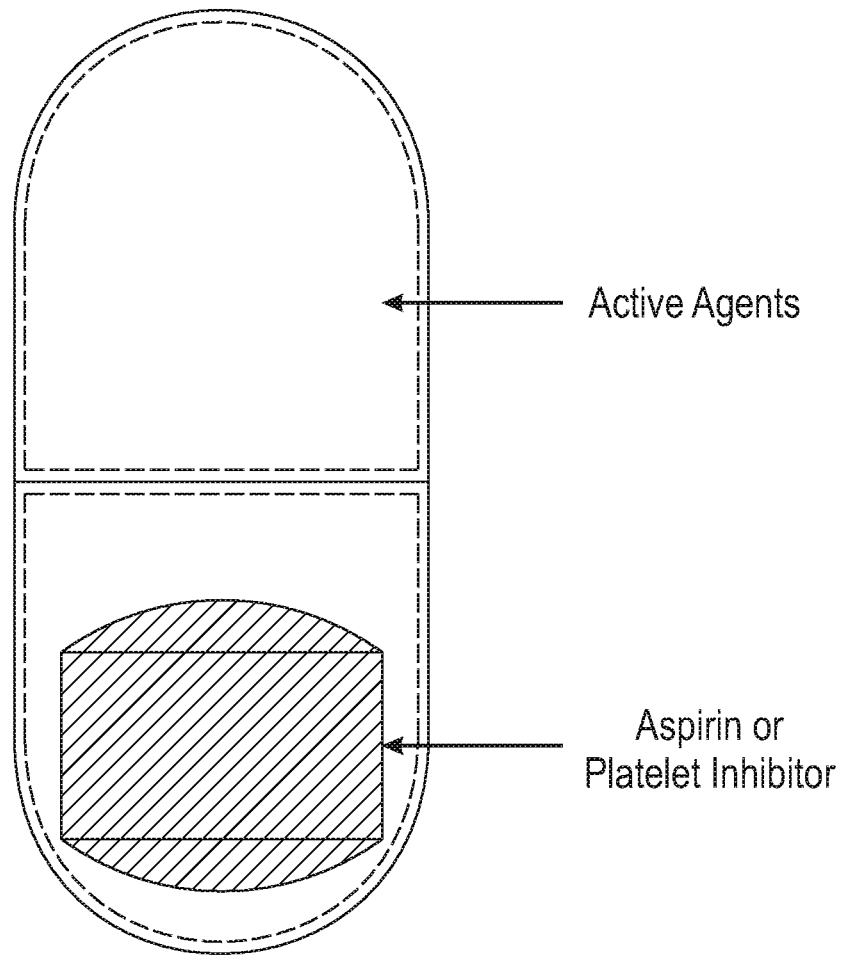
FIG. 1 is a diagram of a combination pharmaceutical dosage form comprising a capsule housing simvastatin and lisinopril and an enteric coated aspirin tablet.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the terms "combination pharmaceutical dosage form," "combination dosage form," "fixed-dose combination," and "fixed-dose combination pharmaceutical" are used interchangeably throughout to refer to a single pharmaceutical product having more than one active agent.

The terms "drug," "active agent," and "agent" are used interchangeably throughout to refer to a pharmaceutical product that has a therapeutic effect.

The term "cardiovascular fixed-dose combination" or "cardiovascular combination" are meant to refer to a combination dosage form comprising an anti-hypertensive agent and a cholesterol-lowering drug.

As used herein, the term "colloidal silica" is meant to refer to any silica or silicon dioxide used in pharmaceutical compounding, including without limitation, "colloidal silicon dioxide," "fumed silica," "hydrophilic fumed silica," and "silica gel."

As used herein, the words "first" and "second" in the terms "a first granulation solution" and "a second granulation solution" are not meant to be limiting with respect to order of preparation. The words "first" and "second" are used only to convey that there are two solutions that have different ingredients and that are applied in a certain order to the methods disclosed herein.

The present invention provides a method for the manufacture of combination dosage forms comprising an anti-hypertensive active agent, a cholesterol-lowering active agent, and optionally, enteric-coated aspirin or an enteric-coated platelet inhibitor. The combination dosage forms are prepared with at least two granulation solutions. The use of the least two granulation solutions to manufacture the combination dosage forms was found to unexpectedly and surprisingly increase the aqueous solubility of the cholesterol-lowering drugs in the fixed dose combinations. As is known to those of skill in the art, the bioavailability of cholesterol-lowering drugs, such as statins, ranges from 5% (e.g., lovastatin and simvastatin) to 60% (e.g., cerivastatin and pitvastatin) with the most effective cholesterol-lowering drugs (i.e., those drugs most effective at reducing low density lipoproteins) generally being on the low end of the bioavailability scale. As is also known to those of skill in the art, drugs that are poorly soluble in water are associated with slower drug absorption, which leads to inadequate and variable bioequivalence. For low-bioavailability cholesterol-lowering drugs, adequate water solubility is necessary to ensure that a sufficient concentration of the active agent enters into systemic circulation to effectuate a pharmacological response. The method disclosed herein results in increased bioavailability of a cholesterol-lowering drug in a fixed-dose combination by enhancing the water-solubility of the cholesterol-lowering drug.

The method disclosed herein also improves the bioavailability of anti-hypertensive drugs in a cardiovascular combination by eliminating the use of acids as a means to stabilize the cholesterol-lowering drugs. Because the addition of stabilizing acids, such as citric acid and sodium citrate, in cardiovascular combinations have been found to cause decomposition of anti-hypertensive agents, such as ACE inhibitors, eliminating the need for such acids results in a cardiovascular combination with improved bioavailability of both the cholesterol-lowering drug and the anti-hypertensive agent.

The anti-hypertensive active agents in the combination dosage forms described herein have the same stability and release profiles as single-formulations comprising the same anti-hypertensive active agents. Similarly, the cholesterol-lowering active agents in the combination dosage forms have the same stability and release profiles as single-formulations comprising the same cholesterol-lowering active agents. The combination dosage forms will be administered once per 24-hour period to an individual in need of an anti-hypertensive drug and a cholesterol-lowering drug.

In one embodiment, an anti-hypertensive drug and a cholesterol-lowering drug are blended in a first granulation solution comprising a preservative to form a granulated mixture and a second granulation solution comprising a binder is added to the granulated mixture, wherein the blending of the cholesterol-lowering drug and the anti-hypertensive drug in the first and second granulation solutions enhances aqueous solubility of the cholesterol-lowering drug in the resulting fixed-dose combination. In a further embodiment, a cholesterol-lowering drug is blended in a first granulation solution comprising a preservative to form a first granulated mixture, an anti-hypertensive drug is added to the first granulated mixture to form a second granulated mixture, and a second granulation solution comprising a binder is added to the second granulated mixture, wherein the blending of the cholesterol-lowering drug and the anti-hypertensive drug in the first and second granulation solutions enhances aqueous solubility of the cholesterol-lowering drug in the resulting fixed-dose combination. In a further embodiment, a cholesterol-lowering drug is blended in a first granulation solution comprising a preservative to form a first granulated mixture, an anti-hypertensive drug is blended in a second granulation solution comprising a binder to form a second granulated mixture, and the first and second granulated mixtures are blended together, wherein the blending of the cholesterol-lowering drug and the anti-hypertensive drug in the first and second granulation solutions enhances aqueous solubility of the cholesterol-lowering drug in the resulting fixed-dose combination.

Examples of liquids that may be used to prepare the granulation solutions include, without limitation, one or more of water, ethanol, and isopropanol. In a further embodiment, a further granulation solution comprising water and ethanol may be required for thorough granulation of the active agents. In another embodiment, a disintegrant may be added to one or more of the granulation solutions.

Examples of preservatives that may be used in the granulation solutions include, without limitation, one or more of, parabens, acids and their salts, quaternary ammonium compounds, alcohols, biguanides, phenols, and phenolic antioxidants. Examples of parabens include, without limitation, methyl paraben, ethyl paraben, propyl paraben, butyl paraben. Examples of acids and their salts including without limitation, benzoic acid, sodium benzoate, sorbic acid, sodium sorbate, citric acid, sodium citrate, and combinations thereof. Examples of quaternary ammonium compounds include, without limitation, cetrimide, benzalkonium chloride, cetylpyridinum chloride, benzethonium chloride, and combinations thereof. Examples of alcohols include, without limitation, benzyl alcohol, phenylethyl alcohol, bronopol, chlorbutanol, and combinations thereof. Examples of phenols include, without limitation, phenol, m-cresol, 4-chlorbutanol, and combinations thereof. Examples of biguanides include, without limitation, alexidine, chlorhexidine, polyaminopropyl biguanide (PAPB), polyhexamethylene biguanide (PHMB), and combinations thereof. Examples of phenolic antioxidants include, without limitation, butylated-hydroxy-anisole (BHA), butylated hydroxytoluene (BHT), tert-butyl-hydroquinone (TBHQ), 4-hydroxymethyl-2,6-di-tert-butylphenol (HMBP), and combinations thereof. Within the context of the present invention, acid preservatives may have limited application where the anti-hypertensive agent is an ACE inhibitor since acids are known to contribute to degradation of ACE inhibitors. In one embodiment, the granulation solutions and the resulting pharmaceutical dosage form are free of acid preservatives. In another embodiment, the granulation solutions and the resulting pharmaceutical dosage form are free of citric acid and/or sodium citrate preservatives.

Examples of binders that may be used in the granulation solutions include, without limitation, saccharides, polysaccharides and derivatives, sugar alcohols, proteins, synthetic polymers. Examples of saccharide binders include, without limitation, sucrose, lactose, and combinations thereof. Examples of polysaccharides and derivatives include, without limitation, starches, celluloses, microcrystalline celluloses, cellulose ethers, hydroxypropyl cellulose (HPC), and combinations thereof. Examples of sugar alcohols include, without limitation, xylitol, sorbitol, mannitol, maltitol, and combinations thereof. Examples of proteins include, without limitation, gelatin. Examples of synthetic polymers include, without limitation, polyvinyl pyrrolidone (PVP or povidone), polyethylene glycol (PEG), and combinations thereof.

Examples of disintegrants that may be used in the granulation solutions include, without limitation, one or more of, PVP, methyl cellulose, carboxymethyl cellulose, sodium carboxy-methyl cellulose, carmellos sodium, microcrystalline cellulose (MCC), sodium starch glycolate, alginic acid, sodium alginate, sodium starch glycolate, polyplasdones, hydrous aluminum silicate, calcium silicate, partially pre-gelatinized starch, and combinations thereof.

Once the active agents are granulated in the at least two granulation solutions, additional excipients may be added to the granulated active agents to manufacture the combination dosage forms. Examples of such additional excipients include, without limitation, glidants, emulsifying agents, and lubricants. Examples of glidants that may be used in the method described herein include, without limitation, one or more of, talc, magnesium carbonate, silica gel, fumed silica, and colloidal silica. Examples of emulsifying agents that may be used in the method described herein include, without limitation, one or more of gelatin, methyl cellulose, pregelatinized starch, and stearic acid. Examples of lubricants that may be used in the method described herein include, without limitation, one or more of, talc, silica, vegetable stearin, stearic acid, and magnesium stearate. Other excipients that may be added to combination dosage forms are coatings and sweeteners, the use of which is known to those of skill in the art.

In Example 1, powdered cellulose is used as a binder and stearic acid is used as a lubricant. In Examples 2-4, PVP is used as a binder; BHA is used as a preservative; partially pre-gelatinized starch is used as a disintegrant; colloidal silica is used as a glidant; stearic acid and partially pre-gelatinized starch are used as emulsifying agents; and magnesium stearate is used as a lubricant. The specific ingredients used and referenced in Examples 1-4 are exemplary and are not intended to be limiting. As is shown above, and as is appreciated by those of skill in the art, the same pharmaceutical excipients may have different uses and may be used more than once in the preparation of suitable pharmaceutical formulations.

In another embodiment, the anti-hypertensive drug and the cholesterol-lowering drug in the fixed-dose combination each have the same stability as single active agent dosage forms containing the same anti-hypertensive drug or the same cholesterol-lowering drug, respectively. In a further embodiment, the anti-hypertensive drug and the cholesterol-lowering drug in the fixed-dose combination each have release profiles that are as fast as, or faster than, the release profiles of single active agent dosage forms containing the same anti-hypertensive drug or the same cholesterol-lowering drug, respectively.

In another embodiment, the anti-hypertensive drug that may be used in the fixed-dose combination described herein is selected from ACE inhibitors, angiotensin receptor inhibitors, and beta blockers. Examples of ACE inhibitors include without limitation, benazepril, captopril, enalapril, fosinopril, lisinopril, moexipril, perindopril, quinapril, ramipril, trandolapril, and combinations thereof. Examples of angiotensin receptor inhibitors include without limitation, azilsartan, candesartan, eprosartan, irbesartan, telmisartan, valsartan, losartan, olmesartan, entresto, byvalson, and combinations thereof. Examples of beta blockers include without limitation, betaxolol, pindolol, acebutolol, atenolol, bisoprolol fumarate, carvedilol, esmolol, labetalol, metoprolol, nadolol, nebivolol, and combinations thereof.

In a further embodiment, the cholesterol-lowering drug is a statin. Examples of statins include without limitation, atorvastatin, fluvastatin, lovastatin, pravastatin, pitavastatin, simvastatin, rosuvastatin, and combinations thereof. In another embodiment, the cholesterol-lowering drug is a non-statin, examples including without limitation, ezetimibe, gemfibrozil, fenofibric acid, lomitapide, and combinations thereof.

In another embodiment, the anti-hypertensive drug and the cholesterol-lowering drug are both independently present in the pharmaceutical dosage form in a range of 1 mg to 160 mg per unit dose.

In a further embodiment, the fixed-dose combination further comprises aspirin and/or a platelet inhibitor. Examples of platelet inhibitors that may be used in the fixed-dose combination include without limitation, clopidogrel, ticagrelor, prasugrel, dipyridamole, ticlopidine, eptifibatide, and combinations thereof. In another embodiment, the aspirin or the platelet inhibitor is present in the fixed-dose combination in a concentration of 25 mg to 325 mg per unit dose. In a further embodiment, the aspirin is present in the fixed-dose combination in a concentration of 81 mg per unit dose. In another embodiment, the aspirin or the platelet inhibitor are enteric coated. Enteric coatings are made with one or more of the following materials: fatty acids, waxes, shellacs, plastics, and plant fibers. Examples of materials used for enteric coatings include without limitation, one or more of, methyl acrylate-methacrylic acid copolymers, cellulose acetate phthalate (CAP), cellulose acetate succinate, hydroxypropyl methyl cellulose phthalate, hydroxypropyl methyl cellulose acetate succinate, polyvinyl acetate phthalate (PVAP), methyl methacrylate-methacrylic acid copolymers, shellac, cellulose acetate trimellitate, sodium alginate, and zein.

In another embodiment, the combination dosage form is a capsule encasing the anti-hypertensive agent, the cholesterol-lowering drug, and an enteric coated aspirin tablet or an enteric coated platelet inhibitor tablet. FIG. 1 shows a representative, but non-limiting, diagram of a capsule having a fixed-dose combination of simvastatin and lisinopril granules with an enteric-coated aspirin tablet encased within the capsule and surrounded by the simvastatin and lisinopril granules.

In a further embodiment, the combination dosage form is a tablet. In one embodiment, the tablet comprises a core and an immediate release outer layer, wherein the core of the tablet is enteric coated aspirin and the immediate release outer layer is comprised of the individual granules comprising the anti-hypertensive drug, the cholesterol-lowering drug, or a combination of the anti-hypertensive drug and the cholesterol-lowering drug. In another embodiment, the tablet comprises a core and an immediate release outer layer, wherein the core of the tablet is an enteric coated platelet inhibitor and the immediate release outer layer is comprised of the individual granules comprising anti-hypertensive drug, the cholesterol-lowering drug, or a combination of the anti-hypertensive drug and the cholesterol-lowering drug.

Table 1 outlines representative, but non-limiting, steps for manufacturing enteric-coated aspirin or enteric-coated platelet inhibitor tablets for use in the combination dosage forms. Example 1 follows the general outline of Table 1, but with specific ingredients to prepare enteric coated aspirin for use in a combination dosage form.

TABLE 1

| Step | Process | Description |
|---|---|---|
| 1. | Preparation of Active Agent, Preparation of Binder, and Screening | Aspirin or a platelet inhibitor and separately a binder are passed through a mesh screen. |
| 2. | Blending of Active Agent and Binder | The screened aspirin or platelet inhibitor and the screened binder are blended. |
| 3. | Preparation and Addition of Lubricant | A lubricant is passed through a mesh screen and added to the blended mixture of Step 2. |
| 4. | Compression | The blend of Step 3 is compressed into tablets. |
| 5. | Clear Coating | A non-enteric coating is applied to the tablets as an undercoat. |
| 6. | Enteric Coating | An enteric coating is applied to the tablets. |
| 7. | Clear Coating | A non-enteric coating (can be the same or different from that in Step 5) is applied to the tablets as an overcoat. |

Tables 2-4 outline representative, but non-limiting, steps for manufacturing a combination pharmaceutical dosage form comprising an anti-hypertensive and a cholesterol-lowering agent according to the method disclosed herein. Table 2 describes the preparation of a fixed-dose combination where the active agents are granulated together in a first granulation solution comprising a preservative followed by the addition of a second granulation solution comprising a binder to form a granulated mixture of the two active agents. Tables 3 and 4 describe the preparation of fixed-dose combinations where the active agents are granulated separately. In Table 3, the anti-hypertensive agent is granulated without a solution and subsequently added to a solution of the cholesterol-lowering drug in a first granulation solution comprising a preservative. A second granulation solution comprising a binder is added to the granulated active agent mixture. In Table 5, the anti-hypertensive agent is granulated in a solution comprising a binder and the cholesterol-lowering drug is separately granulated in a solution comprising a preservative. The two granulation solutions with the separate active agents are combined to form a granulated mixture of the two active agents. Examples 2-4 follow the general outlines of Tables 2-4, respectively.

TABLE 2

| Step | Process | Description |
|---|---|---|
| 1. | Preparation of Binder Solution | A binder is dissolved in a liquid and set aside. |
| 2. | Preparation of Preservative Solution | A preservative is dissolved in a separate liquid and set aside. |
| 3. | Active Agent Granulation and Addition of Preservative Solution | The anti-hypertensive and cholesterol-lowering agents are mixed together in a high shear granulator to form a granulated mixture to which the preservative solution is added. |
| 4. | Addition of Binder Solution and Disintegrant; Densification | The binder solution and a disintegrant are added to the two active agents and the preservative solution in the high shear granulator with mixing. The granulation is discharged when the mixing is complete and the contents of the granulator is a damp densified material. |
| 5. | Screening | The damp densified material is passed through a mesh screen. |
| 6. | Drying | The damp densified material is dried in an oven. |
| 7. | Screening; Preparation of Glidant/Emulsifying Agents. | The dried densified material is screened and milled. Separately, a glidant and emulsifying agent are passed through a mesh screen. |
| 8. | Addition of Glidant/Emulsifying Agent; Blending | The screened dried densified material and the glidant and emulsifying agent are blended together. |
| 9. | Preparation and Addition of lubricant | A lubricant is passed through a mesh screen and added to the blended material of Step 8 with mixing. |
| 10. | Encapsulation | The final blend of the combination pharmaceutical dosage form is encapsulated. Where the capsules are to include aspirin or a platelet inhibitor, the enteric-coated aspirin or platelet inhibitor tablets from Table 1 are included in the encapsulation. |

TABLE 3

| Step | Process | Description |
|---|---|---|
| 1. | Preparation of Binder Solution | A binder is dissolved in a liquid and set aside. |
| 2. | Preparation of Preservative Solution | A preservative is dissolved in a separate liquid and set aside. |
| 3. | Preparation of Anti-hypertensive Agent | The anti-hypertensive agent is granulated in a high shear granulator and set aside. |
| 4. | Preparation of Cholesterol-lowering Agent and Addition of Preservative Solution | The cholesterol-lowering agent is granulated in a high shear granulator and the preservative solution is added to the granulated mixture. |
| 5. | Addition of Anti-hypertensive Agent | The granulated anti-hypertensive agent is added to the granulated cholesterol-lowering agent-preservative mixture. |
| 6. | Addition of Binder Solution and Disintegrant; Densification | The binder solution and a disintegrant are added to the two active agents and the preservative solution in the high shear granulator with mixing. The granulation is discharged when the mixing is complete and the contents of the granulator is a damp densified material. |
| 7. | Screening | The damp densified material is passed through a mesh screen. |
| 8. | Drying | The damp densified material is dried in an oven. |
| 9. | Screening; Preparation of Glidant/Emulsifying Agent. | The dried densified material is passed through a screen mill. Separately, a glidant and emulsifying agent are passed through a mesh screen. |
| 10. | Addition of Glidant/Emulsifying Agent; Blending | The screened dried densified material and the glidant/emulsifying agent are blended together. |
| 11. | Preparation and Addition of lubricant | A lubricant is passed through a mesh screen and added to the blended material of Step 10 with mixing. |
| 12. | Encapsulation | The final blend of the combination pharmaceutical dosage form is encapsulated. Where the capsules are to include aspirin or a platelet inhibitor, the enteric-coated aspirin or platelet inhibitor tablets from Table 1 are included in the encapsulation. |

TABLE 4

| Step | Process | Description |
|---|---|---|
| 1. | Preparation of Binder Solution | A binder is dissolved in a liquid and set aside. |
| 2. | Preparation of Preservative Solution | A preservative is dissolved in a separate liquid and set aside. |
| 3. | Preparation of Anti-hypertensive Agent and Addition of Binder Solution | The anti-hypertensive agent is granulated in a high shear granulator and the binder solution is added to the granulated anti-hypertensive agent. When sufficiently mixed, the granulated mixture of the anti-hypertensive agent and binder solution is set aside. |
| 4. | Preparation of Cholesterol-lowering Agent and Addition of Preservative Solution | The cholesterol-lowering agent is granulated in a high shear granulator and the preservative solution is added to the granulated cholesterol-lowering agent mixture. |
| 5. | Addition of Anti-hypertensive Agent/Binder and a Disintegrant to the Cholesterol-lowering Agent/Preservative; Densification | The granulated anti-hypertensive agent/binder mixture and a disintegrant are added to the granulated cholesterol-lowering agent/preservative mixture in the high shear granulator with mixing. The granulation is discharged when the mixing is complete and the contents of the granulator is a damp densified material. |
| 6. | Screening | The damp densified material is passed through a mesh screen. |
| 7. | Drying | The damp densified material is dried in an oven. |
| 8. | Screening; Preparation of Glidant/Emulsifying Agent. | The dried densified material is passed through a screen mill. Separately, a glidant and emulsifying agent(s) are passed through a mesh screen. |
| 9. | Addition of Glidant/Emulsifying Agent; Blending | The screened dried densified material and the glidant/emulsifying agent(s) are blended together. |
| 10. | Preparation and Addition of lubricant | A lubricant is passed through a mesh screen and added to the blended material of Step 9 with mixing. |
| 11. | Encapsulation | The final blend of the combination pharmaceutical dosage form is encapsulated. Where the capsules are to include aspirin or a platelet inhibitor, the enteric-coated aspirin or platelet inhibitor tablets from Table 1 are included in the encapsulation. |

Figure 2:
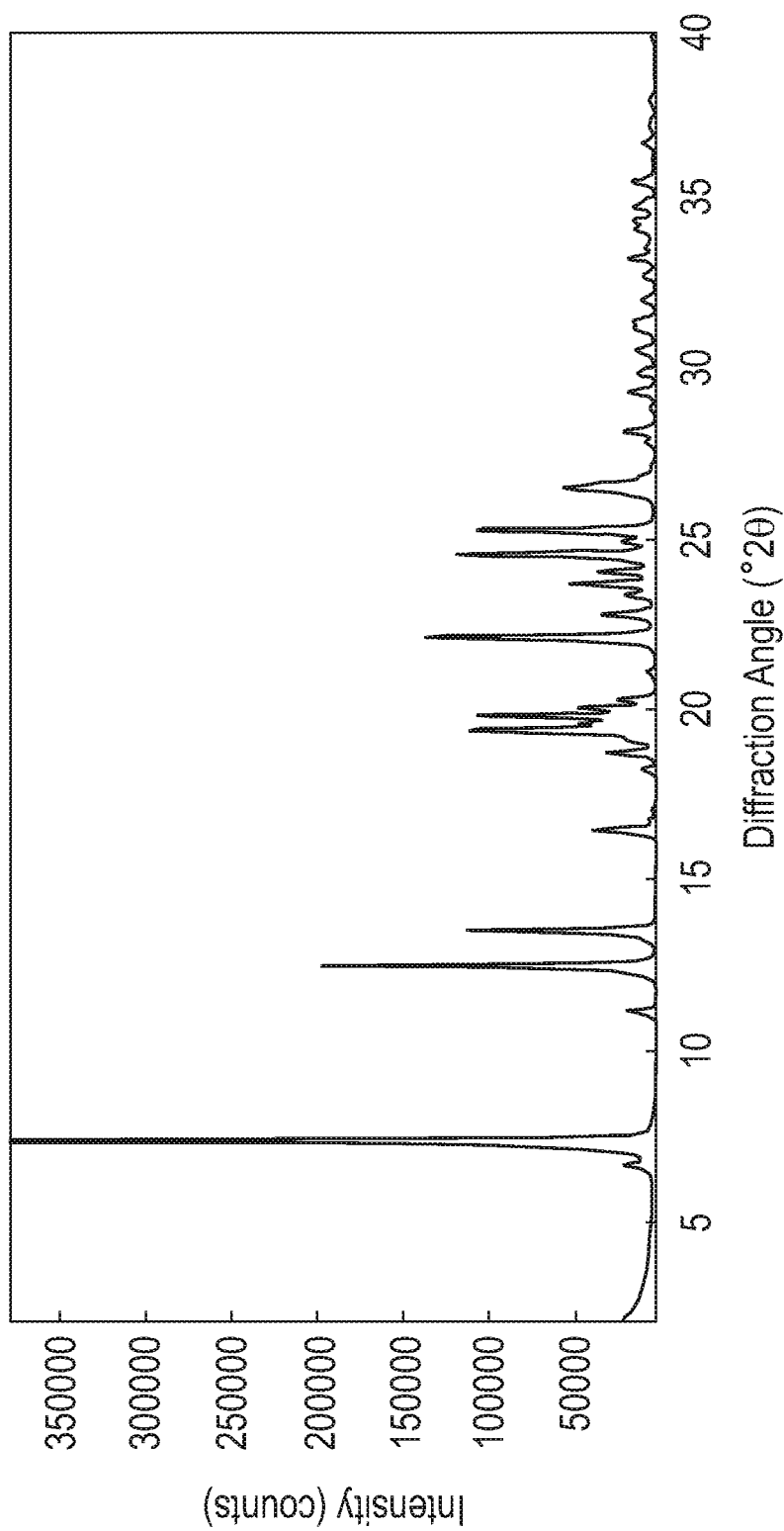
FIG. 2 is a graph showing the x-ray powder diffraction (XRPD) pattern of lisinopril.
Figure 3:
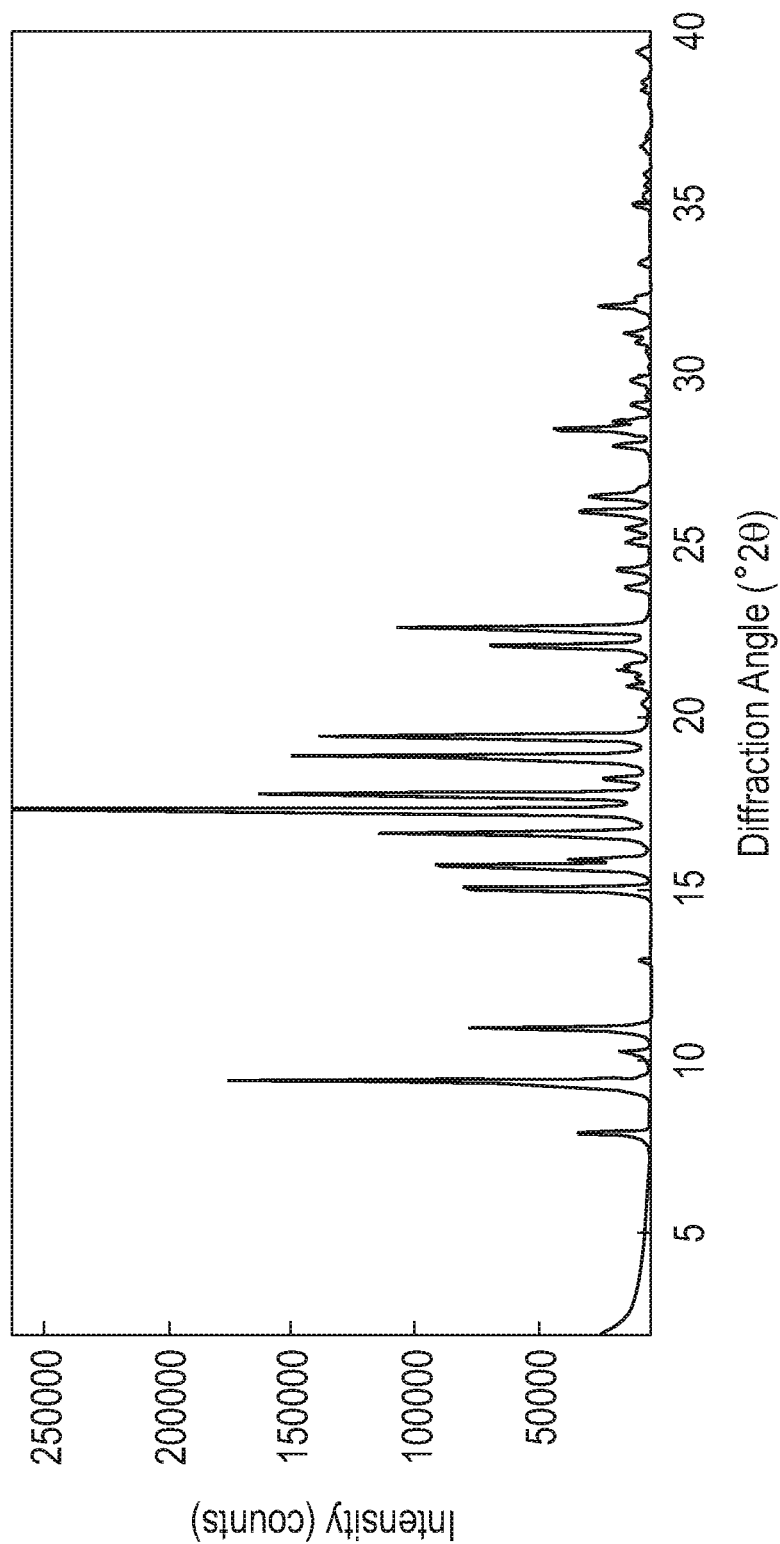
FIG. 3 is a graph showing the XRPD pattern of simvastatin.
Figure 4A:
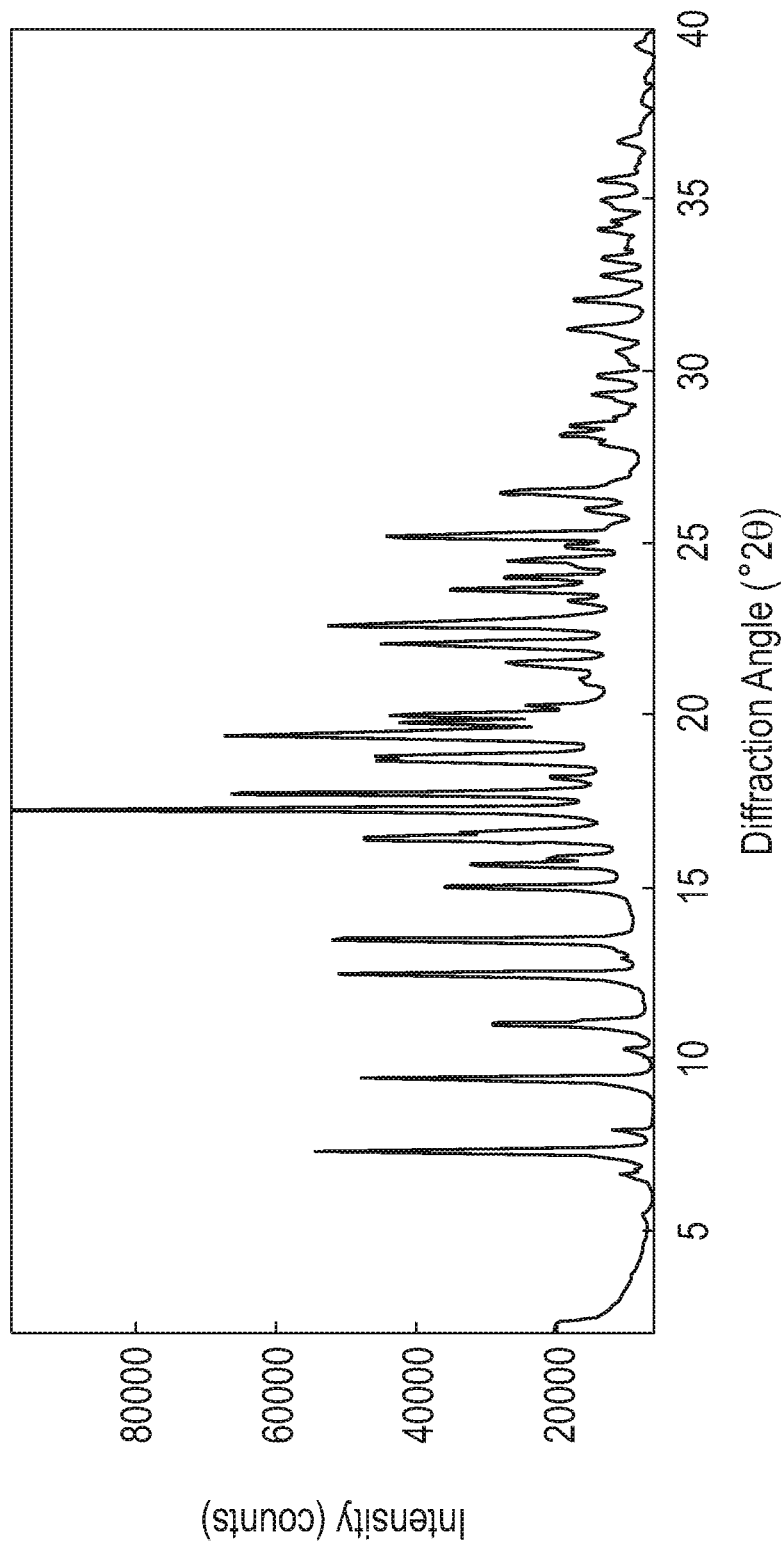
Figure 4B:
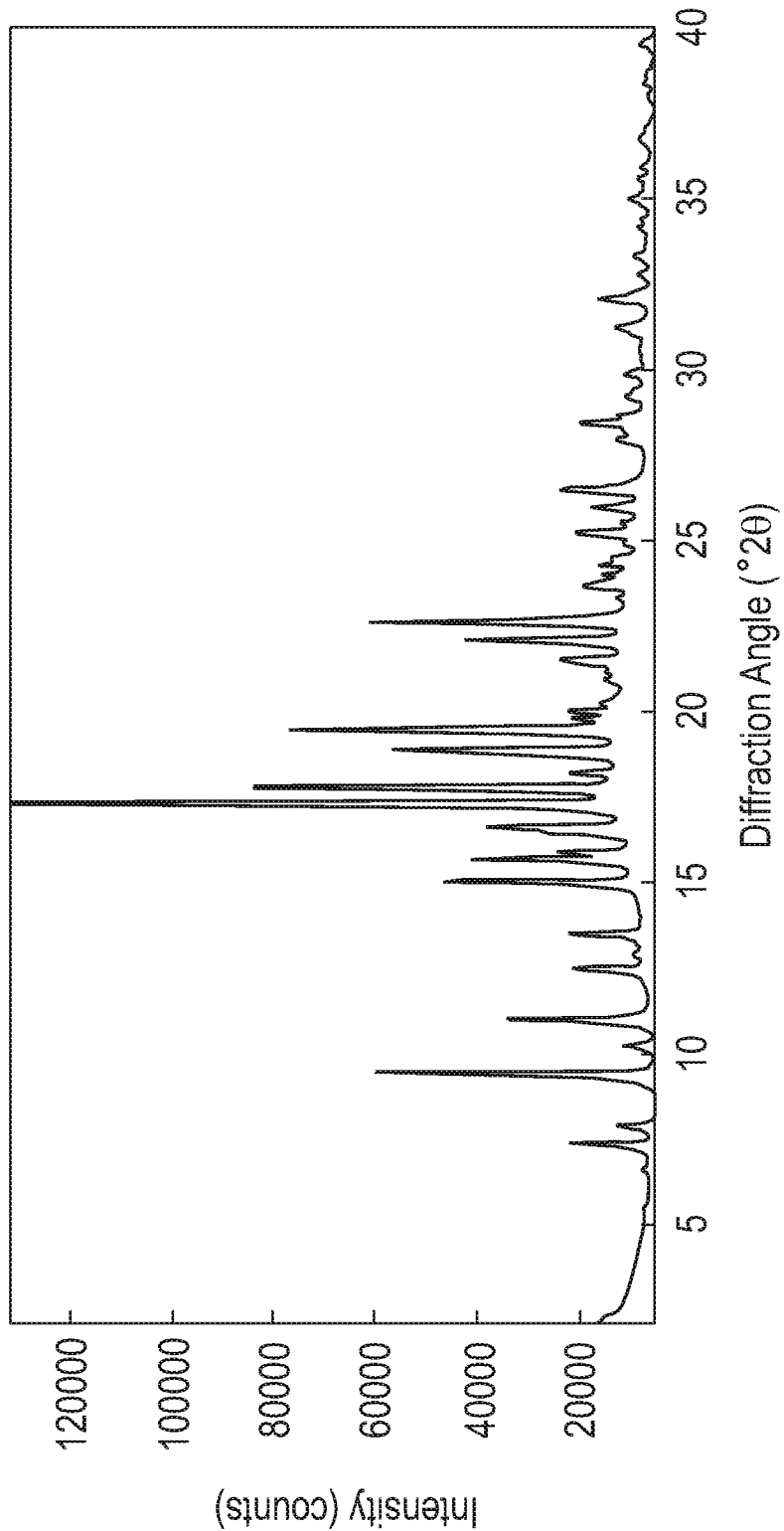
Figure 4C:
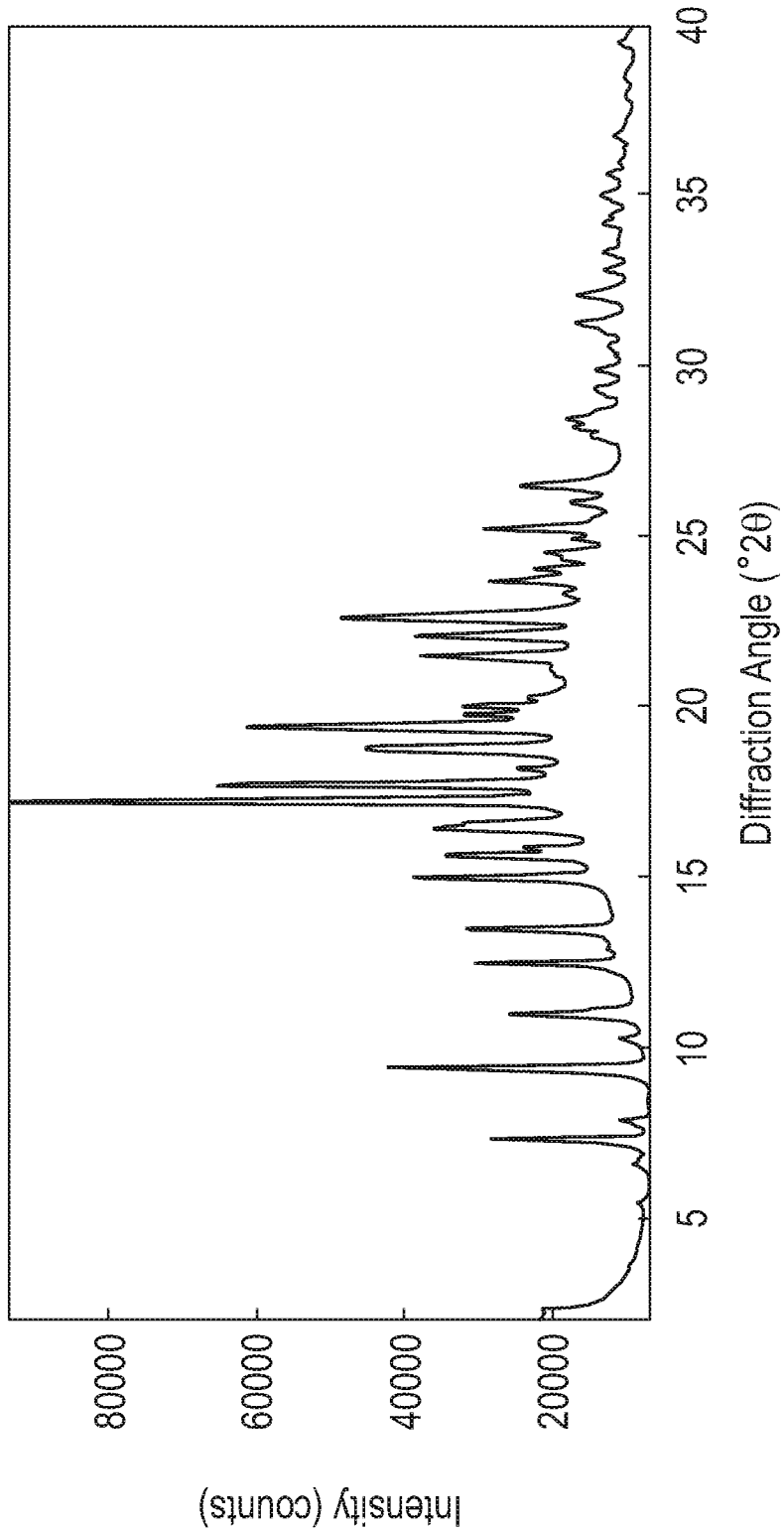
Figure 5:
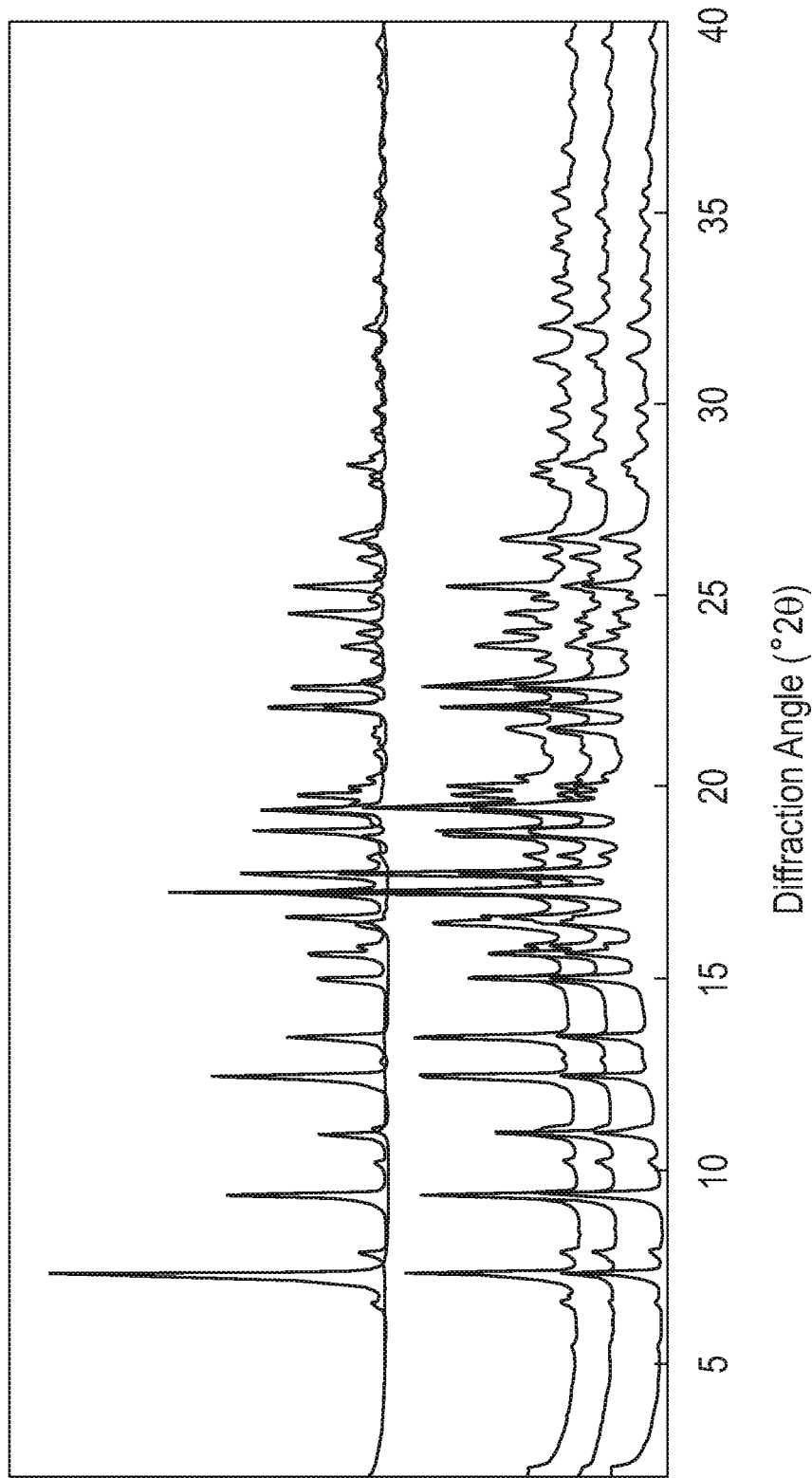
FIG. 5 shows an overlay of the XRPD patterns of FIGS. 4A-4C.

FIG. 2 shows the x-ray powder diffraction (XRPD) pattern for lisinopril and FIG. 3 shows the XPRD pattern for simvastatin. FIG. 4A-4C shows XRPD patterns for the following simvastatin/lisinopril/aspirin fixed-dose combinations, which were prepared according to the method outlined in Table 2: simvastatin/lisinopril/aspirin 20/20/81 mg (FIG. 4A); simvastatin/lisinopril/aspirin 40/10/81 mg (FIG. 4B); and simvastatin/lisinopril/aspirin 40/20/81 mg (FIG. 4C). FIG. 5 shows an overlay of the release profiles of FIGS. 2, 3, and 4A-4C. The lisinopril and simvastatin release profiles are shown in the middle of the graph. The fixed-dose combination release profiles are shown at the bottom of the graph with the simvastatin/lisinopril/aspirin 20/20/81 mg fixed dose combination release profile of FIG. 4A shown at the bottom of the graph; the simvastatin/lisinopril/aspirin 40/10/81 mg fixed dose combination release profile of FIG. 4B shown above the release profile of FIG. 4A; and the simvastatin/lisinopril/aspirin 40/20/81 mg fixed dose combination release profile of FIG. 4C shown above the release profile of FIG. 4B. FIG. 5 shows that the three fixed-dose combination formulations have the same general release profiles (i.e., peak positions and peak areas) as the lisinopril and simvastatin single-dose formulations thus confirming that the individual active agents in the simvastatin/lisinopril/aspirin fixed-dose combinations do not lose their strength when formulated according to the method described herein.

Tables 5-13 show stability data for simvastatin (Tables 5-8), lisinopril (Tables 9-12), and aspirin (Table 13) in the following four different fixed-dose combinations, which were prepared according to the method outlined in Table 2: simvastatin/lisinopril/aspirin 20/10/81 mg; simvastatin/lisinopril/aspirin 20/20/81 mg; simvastatin/lisinopril/aspirin 40/10/81 mg; and simvastatin/lisinopril/aspirin 40/20/81 mg. As shown the tables, all four fixed-dose combinations maintained dissolution stability at 25° C./60% RH (relative humidity) for all three active agents through 24 months of stability testing (RSD=relative standard deviation). At each testing interval, the dissolution of the simvastatin was measured at 45 minutes, the dissolution of the lisinopril was measured at 30 minutes, and the dissolution of the aspirin was measured at 90 minutes.

TABLE 5

| Simvastatin/ Lisinopril/ Aspirin, | % Dissolution of 20 mg of Simvastatin in 45 Minute Following Storage (in Months) of Capsules at 25° C./60% RH | | | | | | |
|---|---|---|---|---|---|---|---|
| 20/10/81 mg Capsules | 0 (Start) | 3 Months | 6 Months | 9 Months | 12 Months | 18 Months | 24 Months |
| 1 | 90 | 96 | 96 | 89 | 94 | 99 | 95 |
| 2 | 94 | 95 | 94 | 103 | 99 | 98 | 100 |
| 3 | 95 | 97 | 89 | 101 | 96 | 98 | 96 |
| 4 | 97 | 102 | 94 | 101 | 100 | 99 | 99 |
| 5 | 97 | 98 | 97 | 103 | 97 | 100 | 99 |
| 6 | 88 | 98 | 96 | 99 | 96 | 100 | 96 |
| Mean of 6 capsules | 94 | 98 | 94 | 99 | 97 | 99 | 98 |
| % RSD | 4.0% | 2.5% | 3.0% | 5.3% | 2.3% | 0.9% | 2.1% |

TABLE 6

| Simvastatin/Lisinopril/Aspirin, 20/20/81 mg Capsules | % Dissolution of 20 mg of Simvastatin in 45 Minutes Following Storage (in Months) of Capsules at 25° C./60% RH ||||||| 
|---|---|---|---|---|---|---|---|
| | 0 (Start) | 3 Months | 6 Months | 9 Months | 12 Months | 18 Months | 24 Months |
| 1 | 103 | 103 | 105 | 98 | 99 | 100 | 97 |
| 2 | 105 | 89 | 98 | 101 | 101 | 105 | 100 |
| 3 | 103 | 98 | 101 | 97 | 102 | 92 | 103 |
| 4 | 92 | 104 | 105 | 103 | 101 | 104 | 93 |
| 5 | 95 | 90 | 106 | 104 | 98 | 99 | 96 |
| 6 | 95 | 104 | 99 | 102 | 85 | 81 | 92 |
| Mean of 6 capsules | 99 | 98 | 102 | 101 | 98 | 97 | 97 |
| % RSD | 5.5% | 7.1% | 3.4% | 2.8% | 6.5% | 9.3% | 4.3% |

TABLE 7

| Simvastatin/Lisinopril/Aspirin, 40/10/81 mg Capsules | % Dissolution of 40 mg of Simvastatin in 45 Minutes Following Storage (in Months) of Capsules at 25° C./60% RH |||||||
|---|---|---|---|---|---|---|---|
| | 0 (Start) | 3 Months | 6 Months | 9 Months | 12 Months | 18 Months | 24 Months |
| 1 | 94 | 95 | 95 | 95 | 92 | 95 | 96 |
| 2 | 94 | 94 | 97 | 96 | 84 | 98 | 99 |
| 3 | 86 | 90 | 96 | 82 | 94 | 97 | 94 |
| 4 | 93 | 98 | 93 | 89 | 95 | 96 | 92 |
| 5 | 98 | 97 | 96 | 97 | 89 | 93 | 95 |
| 6 | 92 | 95 | 87 | 99 | 96 | 85 | 96 |
| Mean of 6 capsules | 93 | 94 | 94 | 93 | 92 | 94 | 95 |
| % RSD | 4.2% | 2.5% | 3.9% | 6.8% | 4.9% | 5.0% | 2.5% |

TABLE 8

| Simvastatin/Lisinopril/Aspirin, 40/20/81 mg Capsules | % Dissolution of 40 mg of Simvastatin in 45 Minutes Following Storage (in Months) of Capsules at 25° C./60% RH |||||||
|---|---|---|---|---|---|---|---|
| | 0 (Start) | 3 Months | 6 Months | 9 Months | 12 Months | 18 Months | 24 Months |
| 1 | 103 | 103 | 104 | 105 | 105 | 105 | 105 |
| 2 | 109 | 107 | 107 | 106 | 106 | 107 | 104 |
| 3 | 105 | 103 | 108 | 107 | 106 | 104 | 102 |
| 4 | 107 | 104 | 109 | 99 | 106 | 98 | 105 |
| 5 | 104 | 103 | 107 | 102 | 107 | 104 | 104 |
| 6 | 105 | 102 | 102 | 106 | 109 | 102 | 103 |
| Mean of 6 capsules | 106 | 104 | 106 | 104 | 107 | 103 | 104 |
| % RSD | 4.0% | 2.5% | 3.0% | 5.3% | 2.3% | 0.9% | 2.1% |

TABLE 9

| Simvastatin/Lisinopril/Aspirin, 20/10/81 mg Capsules | % Dissolution of 10 mg of Lisinopril in 30 minutes Following Storage (in Months) of capsules at 25 25° C./60% RH |||||||
|---|---|---|---|---|---|---|---|
| | 0 (Start) | 3 Months | 6 Months | 9 Months | 12 Months | 18 Months | 24 Months |
| 1 | 101 | 104 | 102 | 104 | 100 | 101 | 101 |
| 2 | 102 | 106 | 102 | 100 | 101 | 102 | 101 |
| 3 | 105 | 105 | 102 | 105 | 102 | 100 | 101 |
| 4 | 99 | 103 | 102 | 104 | 101 | 102 | 101 |

TABLE 9-continued

| Simvastatin/Lisinopril/Aspirin, 20/10/81 mg Capsules | % Dissolution of 10 mg of Lisinopril in 30 minutes Following Storage (in Months) of capsules at 25 25° C./60% RH | | | | | | |
|---|---|---|---|---|---|---|---|
| | 0 (Start) | 3 Months | 6 Months | 9 Months | 12 Months | 18 Months | 24 Months |
| 5 | 100 | 106 | 105 | 103 | 102 | 101 | 101 |
| 6 | 106 | 106 | 105 | 101 | 100 | 102 | 100 |
| Mean of 6 capsules | 102 | 105 | 103 | 103 | 101 | 101 | 101 |
| % RSD | 2.7% | 1.2% | 1.5% | 1.9% | 0.9% | 0.8% | 0.5% |

TABLE 10

| Simvastatin/Lisinopril/Aspirin, 20/20/81 mg Capsules | % Dissolution of 20 mg of Lisinopril in 30 minutes Following Storage (in Months) of capsules at 25° C./60% RH | | | | | | |
|---|---|---|---|---|---|---|---|
| | 0 (Start) | 3 Months | 6 Months | 9 Months | 12 Months | 18 Months | 24 Months |
| 1 | 104 | 105 | 107 | 105 | 103 | 107 | 106 |
| 2 | 105 | 107 | 105 | 106 | 105 | 103 | 106 |
| 3 | 107 | 101 | 109 | 105 | 104 | 106 | 107 |
| 4 | 105 | 107 | 108 | 106 | 104 | 105 | 106 |
| 5 | 107 | 105 | 107 | 102 | 102 | 108 | 105 |
| 6 | 106 | 101 | 105 | 104 | 102 | 106 | 103 |
| Mean of 6 capsules | 106 | 104 | 107 | 105 | 103 | 106 | 105 |
| % RSD | 1.1% | 2.6% | 1.5% | 1.4% | 1.2% | 1.6% | 1.2% |

TABLE 11

| Simvastatin/Lisinopril/Aspirin, 40/10/81 mg Capsules | % Dissolution of 10 mg of Lisinopril in 30 minutes Following Storage (in Months) of capsules at 25° C./60% RH | | | | | | |
|---|---|---|---|---|---|---|---|
| | 0 (Start) | 3 Months | 6 Months | 9 Months | 12 Months | 18 Months | 24 Months |
| 1 | 96 | 102 | 101 | 103 | 101 | 102 | 99 |
| 2 | 100 | 103 | 103 | 103 | 104 | 105 | 102 |
| 3 | 99 | 102 | 100 | 100 | 99 | 105 | 99 |
| 4 | 99 | 101 | 102 | 102 | 104 | 104 | 99 |
| 5 | 99 | 101 | 101 | 103 | 104 | 103 | 100 |
| 6 | 99 | 99 | 100 | 101 | 102 | 105 | 101 |
| Mean of 6 capsules | 99 | 101 | 101 | 102 | 102 | 104 | 100 |
| % RSD | 1.4% | 1.3% | 1.2% | 1.2% | 2.0% | 1.2% | 1.3% |

TABLE 12

| Simvastatin/Lisinopril/Aspirin, 40/20/81 mg Capsules | % Dissolution of 20 mg of Lisinopril in 30 minutes Following Storage (in Months) of capsules at 25° C./60% RH | | | | | | |
|---|---|---|---|---|---|---|---|
| | 0 (Start) | 3 Months | 6 Months | 9 Months | 12 Months | 18 Months | 24 Months |
| 1 | 110 | 106 | 98 | 107 | 105 | 104 | 106 |
| 2 | 108 | 107 | 108 | 110 | 102 | 107 | 102 |
| 3 | 105 | 105 | 108 | 109 | 107 | 102 | 109 |
| 4 | 107 | 108 | 108 | 99 | 107 | 102 | 106 |
| 5 | 108 | 98 | 99 | 104 | 105 | 106 | 105 |
| 6 | 107 | 109 | 108 | 108 | 110 | 99 | 104 |
| Mean of 6 capsules | 108 | 106 | 105 | 106 | 106 | 103 | 105 |
| % RSD | 1.5% | 3.7% | 4.7% | 3.8% | 2.5% | 2.8% | 2.2% |

TABLE 13

| Simvastatin/Lisinopril/Aspirin, 40/20/81 mg Capsules | % Dissolution of 81 mg of Aspirin in 90 minutes Following Storage (in Months) of capsules at 25° C./60% RH | | | | | | |
|---|---|---|---|---|---|---|---|
| | 0 (Start) | 3 Months | 6 Months | 9 Months | 12 Months | 18 Months | 24 Months |
| 1 | 98 | 100 | 99 | 99 | 98 | 100 | 102 |
| 2 | 95 | 96 | 98 | 97 | 97 | 97 | 93 |
| 3 | 100 | 97 | 97 | 101 | 96 | 96 | 93 |
| 4 | 93 | 96 | 97 | 95 | 101 | 101 | 98 |
| 5 | 96 | 98 | 98 | 100 | 100 | 100 | 98 |
| 6 | 99 | 98 | 94 | 99 | 102 | 94 | 97 |
| Mean of 6 capsules | 97 | 98 | 97 | 99 | 99 | 98 | 97 |
| % RSD | 2.7% | 1.6% | 1.8% | 2.2% | 2.4% | 2.8% | 3.5% |

It is to be understood that while the invention has been described in conjunction with the embodiments set forth above, the foregoing description as well as the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

EXAMPLE 1

Preparation Of Enteric-Coated Aspirin Tablets 90 kg of Acetylsalicylic Acid (RHODINE® 2368, Rhodia Chimie Corp., Boulogne, France) was passed through a #20 mesh screen (Erweka GmbH, Germany) with an oscillator and the screened acetylsalicylic acid was set aside. Separately, 6300 g of powdered cellulose (ELCEMA™ Type G 250, Degussa AG, Frankfurt, Germany) was passed through a #20 mesh screen with an oscillator and the screened powdered cellulose was set aside. The screened acetylsalicylic acid and the screened powdered cellulose were blended together in a V-blender (Patterson Kelley 3 cubic foot blender, Keith Machinery Corp., New York, USA) and mixed for 15 minutes (blender speed 20 rpm; I-bar off). Next, 700 g of stearic acid (HYSTRENE® 5016, PMC Biogenix, Inc. Memphis, Tenn., USA) was passed through a #30 mesh screen (Newark Wire Cloth Company, N.J., USA) and added to the mixture in the V-blender and mixed for approximately six minutes (blender speed 20 rpm; I-bar off). The mixture was discharged from the V-blender and compressed into tablets (Kikusui Libra tablet press, Kikusui Seisakusho Limited, Kyoto Japan). The following coatings were added to the tablets in order: OPADRY® Clear (BPSI Holdings, LLC, Del., USA) was applied to the tablets as an undercoat; ACRYL-EZE® (BPSI Holdings, LLC, Del., USA) was applied to the tablets to create the enteric coating; and a second application of OPADRY Clear was applied to the tablets as an overcoat.

EXAMPLE 2

Preparation of Fixed-Dose Simvastatin/Lisinopril Capsules with Co-Granulation of Active Agents 40 mg simvastatin/10 mg lisinopril/81 mg aspirin capsule were prepared as follows.

Granulation Solution Preparation:

3 g of BHA preservative (lab stock, available Sigma Aldrich, St. Louis, Mo., USA) was added to a 250 mL bottle with 128 g of ethanol (200 proof) labeled "BHA Granulation Solution." The contents of the bottle were vigorously mixed for four minutes, and set aside. Separately, 1600 g of purified water was added to a tared SS container labeled "Povidone Granulation Solution" and mixed with an overhead mixer until a vortex was created (approximately one minute) at which time 1600 g of ethanol (200 proof) was added to the container. With continued mixing, 432 g of povidone binder (PLASDONE® K-29/32, ISP Investments LLC, Wilmington, Del., USA) was slowly added to the container with continued mixing at 350 rpm until the povidone had completely dissolved (approximately ten minutes). Another SS container labeled "Additional Granulation Solution" was prepared in case an additional granulation solution was needed during granulation. The "Additional Granulation Solution" was made by mixing 320 g of purified water and 320 g of ethanol (200 proof) in the SS container and mixing for one minute at 100 rpm.

Granulation:

6400 g of simvastatin (Hetero Labs Limited, Hyderabad India) and 1749 g of lisinopril (Farm Hispania S.A., Barcelona Spain) were mixed together for five minutes (impeller speed 300 rpm; chopper speed 1800 rpm) in a 65 L bowl of a high shear granulator (Fiedler PMA 65 25, T.K. Fielder Limited). Next, the pump for the high shear granulator was calibrated to deliver 38 (±15) g/min for the BHA Granulation Solution and 384 g (±15) g/min for the Povidone Granulation. The BHA solution was added to the simvastatin/lisinopril mixture in the 65 L bowl at the rate of 38 g/min with mixing for five minutes (impeller speed 300 rpm; chopper speed off). After the five-minute mixing (and after all of the BHA Granulation Solution was added), the lid of the bowl was opened, the sides of the bowl were scraped, and the bowl was mixed for one additional minute (impeller speed 300 rpm; chopper speed off). Next, 5227 g of partially pre-gelatinized maize starch (STARCH 1500®, BPSI Holdings LLC, Wilmington, Del., USA) was added to the simvastatin/lisinopril/BHA mixture in the 65 L bowl and mixed for two minutes (impeller speed 300 rpm; chopper speed off). The Povidone Granulation Solution was next added to the 65 L bowl at a rate of 384 g/min with mixing (impeller speed 300 rpm; chopper speed 1800 rpm) for approximately 10 minutes. Weight measurements for the mixture were taken every two minutes during the 10-minute run. After the 10-minute mixing (and after all of the Povidone Granulation Solution was added), the lid of the bowl was opened, the sides of the bowl were scraped, and the bowl was mixed for two additional minutes (impeller speed 300 rpm; chopper speed 1800 rpm). As the simvastatin/lisinopril mixture was thoroughly granulated, there was no need for the Additional Granulation Solution.

Next, the granulated simvastatin/lisinopril mixture was discharged from the granulator and passed through a #6 mesh screen (Newark Wire Cloth Company, N.J., USA) and placed into an oven (Gruenberg L18h27-0SS, Gruenberg Oven Company, Pa., USA) for drying at 55-60° C. until the LOD (loss on drying) value was not more than 3.5% (approximately two hours).

After weighing, the dried densified simvastatin/lisinopril material was screened with a #20 mesh screen (Newark Wire Cloth Company, N.J., USA). All material that did not pass through the screening was milled using a Quadro COMIL® 197 (Ultra, Quadro Engineering Corp, Waterloo, Ontario, Canada) equipped with a 991-micron screen (spacer 0.3 in; mill speed 1500 rpm). The screened milled granules were collected, weighed, and tared in a dedicated container labeled "Screened and Milled Granules."

Blending:

Separately, 144 g of colloidal silicon dioxide (CAB-O-SIL® M5-P, Cabot Corp., Boston, Mass., USA) and 311 g of stearic acid (HYSTRENE® 5016, PMC Biogenix, Inc. Memphis, Tenn., USA) were passed through a #20 mesh screen (Newark Wire Cloth Company, N.J., USA). The screened dried densified simvastatin/lisinopril material together with the colloidal silicon dioxide and stearic acid were then blended in a V-blender (Patterson Kelley 1 cubic foot blender, Keith Machinery Corp. New York, USA) for 10 minutes (blender speed 25 rpm; I-bar off). Next, 145 g of magnesium stearate (HYQUAL™, Avantor Performance Materials, LLC Center Valley, Pa., USA) was passed through a #30 mesh screen (Newark Wire Cloth Company, N.J., USA) and added to the V-blender with mixing for three minutes (blender speed 25 rpm; I-bar off). Upon completion of the mixing, blend uniformity samples were taken. The final simvastatin/lisinopril blend was discharged from the V-blender and encapsulated with the enteric-coated aspirin tablets made according to the procedure of Example 1.

EXAMPLE 3

Preparation of Fixed-Dose Simvastatin/Lisinopril Capsules with Separate Granulation of Active Agents The procedure of Example 2 is followed with the following change. In the Granulation step, the lisinopril is granulated in the high shear granulator and is set aside in dry form. The simvastatin is granulated as described in Example 2 and the BHA Granulation Solution is added to the simvastatin mixture with mixing. After the simvastatin is thoroughly mixed, the dry lisinopril is added to the simvastatin mixture with mixing. The remainder of the procedure is as described in Example 2.

EXAMPLE 4

Preparation f Fixed-Dose Simvastatin/Lisinopril Capsules with Separate Granulation of Active Agents The procedure of Example 2 is followed with the following change. In the Granulation step, the simvastatin is granulated in the high shear granulator with the BHA Granulation Solution and separately, the lisinopril is granulated in the high shear granulator with the Povidone Granulation Solution (with one of the two solutions being set aside and the other remaining in the granulator). The two separate granulation solutions are combined together in the high shear granulator with the addition of the pre-gelatinized starch and mixed. The remainder of the procedure is as described in Example 2.

We claim:

1. A method comprising:
    blending a cholesterol-lowering drug and an anti-hypertensive drug in a first granulation solution comprising a preservative to form a first granulated mixture, wherein the first granulation solution does not include a binder;
    adding a second granulation solution comprising a binder to the first granulated mixture to form a second granulated mixture comprising the cholesterol-lowering drug and the anti-hypertensive drug, wherein aqueous solubility of the cholesterol-lowering drug in the second granulated mixture is enhanced relative to a single formulation of a cholesterol-lowering drug;
    drying the second granulated mixture to form individual granules comprising a combination of the cholesterol-lowering drug and the anti-hypertensive drug; and
    forming a pharmaceutical dosage form comprising the individual granules, wherein dissolution of the cholesterol-lowering drug in the pharmaceutical dosage form is ~100% after 45 minutes.

2. The method of claim 1, wherein the preservative is selected from the group consisting of parabens, acids and their salts, quaternary ammonium compounds, alcohols, biguanides, phenols, phenolic antioxidants, and combinations thereof.

3. The method of claim 1, wherein the preservative is solubilized in a liquid selected from the group consisting of water, ethanol, isopropanol, and combinations thereof.

4. The method of claim 1, wherein the first granulation solution comprises butylated-hydroxy-anisole (BHA) solubilized in ethanol.

5. The method of claim 1, wherein the binder is selected from the group consisting of saccharides, polysaccharides and derivatives, sugar alcohols, proteins, synthetic polymers, and combinations thereof.

6. The method of claim 1, wherein the binder is solubilized in a liquid selected from the group consisting of water, ethanol, isopropanol, and combinations thereof.

7. The method of claim 1, wherein the second granulation solution comprises polyvinyl pyrrolidone (PVP) solubilized in a water and ethanol solution.

8. The method of claim 1, wherein the first granulation solution, the second granulation solution, and the pharmaceutical dosage form are free of citric acid.

9. The method of claim 1, wherein the anti-hypertensive drug is selected from the group consisting of angiotensin-converting enzyme (ACE) inhibitors, angiotensin receptor inhibitors, and beta blockers.

10. The method of claim 9, wherein the ACE inhibitors are selected from the group consisting of benazepril, captopril, enalapril, fosinopril, lisinopril, moexipril, perindopril, quinapril, ramipril, trandolapril, and combinations thereof.

11. The method of claim 9, wherein the angiotensin receptor inhibitors are selected from the group consisting of azilsartan, candesartan, eprosartan, irbesartan, telmisartan, valsartan, losartan, olmesartan, entresto, byvalson, and combinations thereof.

12. The method of claim 9, wherein the beta blockers are selected from the group consisting of betaxolol, pindolol, acebutolol, atenolol, bisoprolol fumarate, carvedilol, esmolol, labetalol, metoprolol, nadolol, nebivolol, and combinations thereof.

13. The method of claim 1, wherein the cholesterol-lowering drug is a statin selected from the group consisting of atorvastatin, fluvastatin, lovastatin, pravastatin, pitavastatin, simvastatin, rosuvastatin, and combinations thereof.

14. The method of claim 1, wherein the cholesterol-lowering drug is a non-statin selected from the group consisting of ezetimibe, gemfibrozil, fenofibric acid, lomitapide, and combinations thereof.

15. The method of claim 1, wherein the anti-hypertensive drug is an ACE inhibitor and the cholesterol-lowering drug is a statin.

16. The method of claim 1, wherein the anti-hypertensive drug is lisinopril and the cholesterol-lowering drug is simvastatin.

17. The method of claim 1, wherein the anti-hypertensive drug is present in the pharmaceutical dosage form in a range of 1 mg to 160 mg per unit dose.

18. The method of claim 1, where the cholesterol-lowering drug is present in the pharmaceutical dosage form in a range of 1 mg to 160 mg per unit dose.

19. The method of claim 1, wherein the pharmaceutical dosage form further comprises enteric coated aspirin or an enteric coated platelet inhibitor.

20. The method of claim 19, wherein the enteric coated platelet inhibitor is selected from the group consisting of clopidogrel, ticagrelor, prasugrel, dipyridamole, ticlopidine, eptifibatide, and combinations thereof.

21. The method of claim 19, wherein the enteric coated aspirin or the enteric coated platelet inhibitor is in a concentration of 25 mg to 325 mg per unit dose.

22. The method of claim 19, wherein the enteric coated aspirin is in a concentration of 81 mg per unit dose.

23. The method of claim 1, wherein the pharmaceutical dosage form is a capsule.

24. The method of claim 23, wherein the pharmaceutical dosage form further comprises enteric coated aspirin tablets or an enteric coated platelet inhibitor encased within the capsule.

25. The method of claim 1, wherein the pharmaceutical dosage form is a tablet.

26. The method of claim 25, wherein the tablet comprises a core and an immediate release outer layer, wherein the core of the tablet is enteric coated aspirin and the immediate release outer layer is comprised of the individual granules comprising the anti-hypertensive drug, the cholesterol-lowering drug, or a combination of the anti-hypertensive drug and the cholesterol-lowering drug.

27. The method of claim 25, wherein the tablet comprises a core and an immediate release outer layer, wherein the core of the tablet is an enteric coated platelet inhibitor and the immediate release outer layer is comprised of the individual granules comprising the anti-hypertensive drug, the cholesterol-lowering drug, or a combination of the anti-hypertensive drug and the cholesterol-lowering drug.

28. The method of claim 1, further comprising administering a single dosage of the pharmaceutical dosage form to an individual in need of an anti-hypertensive drug and a cholesterol-lowering drug once per 24-hour period.

29. A method comprising:
blending a cholesterol-lowering drug in a first granulation solution comprising butylated-hydroxy-anisole solubilized in ethanol to form a first granulated mixture, wherein the first granulation solution does not include a binder;
adding a granulated anti-hypertensive drug to the first granulated mixture to form a second granulated mixture;
adding a second granulation solution comprising a binder to the second granulated mixture to form a third granulated mixture comprising the cholesterol-lowering drug and the anti-hypertensive drug, wherein aqueous solubility of the cholesterol-lowering drug in the third granulated mixture is enhanced relative to a single formulation of a cholesterol-lowering drug;
drying the third granulated mixture to form individual granules, wherein each of the individual granules contains the cholesterol-lowering drug, the anti-hypertensive drug, or a combination of the cholesterol-lowering drug and the anti-hypertensive drug; and
forming a pharmaceutical dosage form comprising the individual granules, wherein the dissolution of the cholesterol-lowering drug in the pharmaceutical dosage form is ~100% after 45 minutes.

30. The method of claim 29, wherein the binder is selected from the group consisting of saccharides, polysaccharides and derivatives, sugar alcohols, proteins, synthetic polymers, and combinations thereof.

31. The method of claim 29, wherein the binder is solubilized in a liquid selected from the group consisting of water, ethanol, isopropanol, and combinations thereof.

32. The method of claim 29, wherein the second granulation solution comprises polyvinyl pyrrolidone (PVP) solubilized in a water and ethanol solution.

33. The method of claim 29, wherein the first granulation solution, the second granulation solution, and the pharmaceutical dosage form are free of citric acid.

34. The method of claim 29, wherein the anti-hypertensive drug is selected from the group consisting of angiotensin-converting enzyme (ACE) inhibitors, angiotensin receptor inhibitors, and beta blockers.

35. The method of claim 34, wherein the ACE inhibitors are selected from the group consisting of benazepril, captopril, enalapril, fosinopril, lisinopril, moexipril, perindopril, quinapril, ramipril, trandolapril, and combinations thereof.

36. The method of claim 34, wherein the angiotensin receptor inhibitors are selected from the group consisting of azilsartan, candesartan, eprosartan, irbesartan, telmisartan, valsartan, losartan, olmesartan, entresto, byvalson, and combinations thereof.

37. The method of claim 34, wherein the beta blockers are selected from the group consisting of betaxolol, pindolol, acebutolol, atenolol, bisoprolol fumarate, carvedilol, esmolol, labetalol, metoprolol, nadolol, nebivolol, and combinations thereof.

38. The method of claim 29, wherein the cholesterol-lowering drug is a statin selected from the group consisting of atorvastatin, fluvastatin, lovastatin, pravastatin, pitavastatin, simvastatin, rosuvastatin, and combinations thereof.

39. The method of claim 29, wherein the cholesterol-lowering drug is a non-statin selected from the group consisting of ezetimibe, gemfibrozil, fenofibric acid, lomitapide, and combinations thereof.

40. The method of claim 29, wherein the anti-hypertensive drug is an ACE inhibitor and the cholesterol-lowering drug is a statin.

41. The method of claim 29, wherein the anti-hypertensive drug is lisinopril and the cholesterol-lowering drug is simvastatin.

42. The method of claim 29, wherein the anti-hypertensive drug is present in the pharmaceutical dosage form in a range of 1 mg to 160 mg per unit dose.

43. The method of claim 29, where the cholesterol-lowering drug is present in the pharmaceutical dosage form in a range of 1 mg to 160 mg per unit dose.

44. The method of claim 29, wherein the pharmaceutical dosage form further comprises enteric coated aspirin or an enteric coated platelet inhibitor.

45. The method of claim 44, wherein the enteric coated platelet inhibitor is selected from the group consisting of clopidogrel, ticagrelor, prasugrel, dipyridamole, ticlopidine, eptifibatide and combinations thereof.

46. The method of claim 44, wherein the enteric coated aspirin or the enteric coated platelet inhibitor is in a concentration of 25 mg to 325 mg per unit dose.

47. The method of claim 44, wherein the enteric coated aspirin is in a concentration of 81 mg per unit dose.

48. The method of claim 29, wherein the pharmaceutical dosage form is a capsule.

49. The method of claim 48, wherein the pharmaceutical dosage form further comprises enteric coated aspirin tablets or an enteric coated platelet inhibitor encased within the capsule.

50. The method of claim 29, wherein the pharmaceutical dosage form is a tablet.

51. The method of claim 50, wherein the tablet comprises a core and an immediate release outer layer, wherein the core of the tablet is enteric coated aspirin and the immediate release outer layer is comprised of the individual granules comprising the anti-hypertensive drug, the cholesterol-lowering drug, or a combination of the anti-hypertensive drug and the cholesterol-lowering drug.

52. The method of claim 50, wherein the tablet comprises a core and an immediate release outer layer, wherein the core of the tablet is an enteric coated platelet inhibitor and the immediate release outer layer is comprised of the individual granules comprising the anti-hypertensive drug, the cholesterol-lowering drug, or a combination of the anti-hypertensive drug and the cholesterol-lowering drug.

53. The method of claim 29, further comprising administering a single dosage of the pharmaceutical dosage form to an individual in need of an anti-hypertensive drug and a cholesterol-lowering drug once per 24-hour period.

54. A method comprising:
blending simvastatin and lisinopril in a first granulation solution comprising butylated-hydroxy-anisole (BHA) to form a first granulated mixture, wherein the first granulation solution does not include a binder;
adding a second granulation solution comprising a binder to the first granulated mixture to form a second granulated mixture comprising the simvastatin and the lisinopril, wherein aqueous solubility of the simvastatin in the second granulated mixture is enhanced relative to a single formulation of simvastatin;
drying the second granulated mixture to form individual granules comprising a combination of the simvastatin and the lisinopril; and
forming a pharmaceutical dosage form comprising the individual granules, wherein dissolution of the simvastatin in the pharmaceutical dosage form is ~100% after 45 minutes.

55. The method of claim 54, wherein the BHA is solubilized in ethanol.

56. The method of claim 54, wherein the binder is selected from the group consisting of saccharides, polysaccharides and derivatives, sugar alcohols, proteins, synthetic polymers, and combinations thereof.

57. The method of claim 54, wherein the binder is solubilized in a liquid selected from the group consisting of water, ethanol, isopropanol, and combinations thereof.

58. The method of claim 54, wherein the second granulation solution comprises polyvinyl pyrrolidone (PVP) solubilized in a water and ethanol solution.

59. The method of claim 54, wherein the first granulation solution, the second granulation solution, and the pharmaceutical dosage form are free of citric acid.

60. The method of claim 54, wherein the lisinopril is present in the pharmaceutical dosage form in a range of 1 mg to 160 mg per unit dose.

61. The method of claim 54, where the simvastatin is present in the pharmaceutical dosage form in a range of 1 mg to 160 mg per unit dose.

62. The method of claim 60, wherein the pharmaceutical dosage form further comprises enteric coated aspirin or an enteric coated platelet inhibitor.

63. The method of claim 62, wherein the enteric coated platelet inhibitor is selected from the group consisting of clopidogrel, ticagrelor, prasugrel, dipyridamole, ticlopidine, eptifibatide, and combinations thereof.

64. The method of claim 62, wherein the enteric coated aspirin or the enteric coated platelet inhibitor is in a concentration of 25 mg to 325 mg per unit dose.

65. The method of claim 62, wherein the enteric coated aspirin is in a concentration of 81 mg per unit dose.

66. The method of claim 54, wherein the pharmaceutical dosage form is a capsule.

67. The method of claim 66, wherein the pharmaceutical dosage form further comprises enteric coated aspirin tablets or an enteric coated platelet inhibitor encased within the capsule.

68. The method of claim 54, wherein the pharmaceutical dosage form is a tablet.

69. The method of claim 68, wherein the tablet comprises a core and an immediate release outer layer, wherein the core of the tablet is enteric coated aspirin and the immediate release outer layer is comprised of the individual granules comprising the anti-hypertensive drug, the cholesterol-lowering drug, or a combination of the anti-hypertensive drug and the cholesterol-lowering drug.

70. The method of claim 68, wherein the tablet comprises a core and an immediate release outer layer, wherein the core of the tablet is an enteric coated platelet inhibitor and the immediate release outer layer is comprised of the individual granules comprising the anti-hypertensive drug, the cholesterol-lowering drug, or a combination of the anti-hypertensive drug and the cholesterol-lowering drug.

71. The method of claim 54, further comprising administering a single dosage of the pharmaceutical dosage form to an individual in need of an anti-hypertensive drug and a cholesterol-lowering drug once per 24-hour period.

* * * * *